United States Patent [19]
DeLuca et al.

[11] Patent Number: 5,808,120
[45] Date of Patent: Sep. 15, 1998

[54] METHOD OF SYNTHESIS OF RETINOIC ACID

[75] Inventors: Hector F. DeLuca, Deerfield; Praveen K. Tadikonda, Madison, both of Wis.

[73] Assignee: Wisconsin Alumni Research Foundation, Madison, Wis.

[21] Appl. No.: 517,931

[22] Filed: Aug. 22, 1995

[51] Int. Cl.$^6$ .................................................. C11C 3/00
[52] U.S. Cl. ........................ 554/163; 554/124; 554/132; 554/154; 554/221; 554/224; 252/625; 423/647.7
[58] Field of Search .................................... 554/221, 163, 554/124, 132, 154, 224; 252/625; 423/647.7

[56] References Cited

U.S. PATENT DOCUMENTS 3,928,400  12/1975  Olson et al. ..................... 260/419.9 V

OTHER PUBLICATIONS

Chien et al J Labelled Cpds & Radio pharmaceuticals, XVI(5), pp. 791–797, 1979.
Y. L. Bennani, et al. "Syntheses of High Specific Activity 2,3– and 3,4–[$^3$H]$_2$–9–cis–Retinoic Acid," *J. Org. Chem.* 60:119–1200, 1995.
M. F. Boehm, et al., "Synthesis of High Specific Activity [$^3$H]–9–cis–Retinoic Acid and Its Application for Identifying Retinoids with Unusual Binding Properties," *J. Med. Chem.* 37:408–414, 1994.
P.–L. Chien, et al., "Synthesis of 13–cis–(11–$^3$H)–Retinoic Acid," *Journal of Labelled Compounds and Radiopharmaceuticals* XVI(5):791–797, 1979.
P.–L. Chien, et al., "Synthesis of trans–[11–$^3$H]–Retinoic Acid and its 5,6–Epoxide," *Journal of Labelled Compounds and Radiopharmaceuticals* XVII(5):759–762, 1979.
M. I. Dawson, et al., "Preparation of 9–cis–Retinoic Acid [11,12–$^3$H(N)] by Photochemical Isomerization," *Journal of Labelled Compounds and Radiopharmaceuticals* XXXIII (3):245–247, 1992.
A. R. de Lera, et al., "Stereospecific Synthesis of 9–Demethylretinoids via Palladium–Catalyzed Vinylboronic Acid––Vinyl Iodide Cross Coupling," *Tetrahedron Letters* 33(41):6205–6208, 1992.
H. H. Kaegi, et al., "Preparation of all Trans–Retinoic–11–$^3$H Acid and all Trans–Retinyl–11–$^3$H Acetate," *Journal of Labelled Compounds and Radiopharmaceuticals* XVIII(8):1099–1106, 1980.
A. A. Liebman, et al., "The Synthesis of Isotopically Labeled Retinoids," *Journal of Labelled Compounds and Radiopharmaceuticals* XXVIII(5):525–541, 1989.
P. J. van den tempel, et al., "Vitamin A Analogues—V, Synthesis of 9–, 13–, and 9,13–Desmethyl Homologues of Vitamin A," *Tetrahedron* 22:293–299, 1966.
1995 Catalog, Amerisham Life science, p. 364.
Tanaka et al., Journal of Med. Chem, vol. 35, pp. 567–572, 1992.
Bennani et al., Journal of Org. Chem. vol. 60, pp. 1195–1200, 1995.

*Primary Examiner*—Paul J. Killos
*Assistant Examiner*—Deborah D. Carr
*Attorney, Agent, or Firm*—Quarles & Brady

[57] ABSTRACT

A method of synthesizing 9-cis-retinoic acid, all-trans-retinoic acid or 9-nor-retinoic acid is disclosed. The method comprises the steps of adding a Grignard reagent of

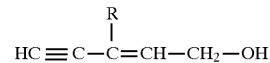

to 2,2,6 trimethyl cyclohexanone is disclosed. R is a methyl group or H and the $CH_2$—OH group is in either the cis or trans orientation relative to the HC≡C- group. The resulting product is converted into retinoic acid. In the preferable form of the present invention, a tritium-labelled retinoic acid is synthesized, wherein the labelling is at the $C_{20}$ position. A preparation of tritium-labelled 9-cis-retinoic acid with a specific activity of greater than 65 Ci/mmol is also enclosed. In a most preferred embodiment, the specific activity is greater than 75 Ci/mmol.

13 Claims, 3 Drawing Sheets

Reagents: a. EtMgBr, THF  b. LAH, THF  c. MnO$_2$, DCM  d. Ph$_3$P=CHCOOMe, Benzene  e. HCOOH, Hexane  f. DIBAL-H, DCM,-78°C  g. $^n$H$_3$CMgBr,THF  h. (EtO)$_2$P(O)CH$_2$COOMe, NaH, THF  i. aq. KOH, MeOH, 50°C.

Reagents: a. EtMgBr, THF, b. LAH, THF, c. $MnO_2$, DCM, d. $Ph_3P=CHCOOMe$,
Benzene, e. HCOOH, Hexane, f. DIBAL-H, DCM, -78°C, g. $^nH_3CMgX$, THF
h. $(Et)_2P(O)CH_2COOMe$, THF, NaH, i. aq. KOH, MeOH, 50°C.

METHOD OF SYNTHESIS OF RETINOIC ACID

FIELD OF THE INVENTION

The present invention is generally directed to methods of synthesizing retinoic acid. In particular, the present invention is directed to methods of synthesizing 9-cis- retinoic acid, 9-trans-retinoic acid, 9-nor-retinoic acid and labelled versions of these compounds.

BACKGROUND

Retinoids are an important class of compounds known for their role in mediating cell growth, differentiation of epithelial tissues, visual function and reproduction. Retinoic acids, one form of retinoid, are currently being studied for roles in cell growth and differentiation. All-trans-retinoic acid is currently in clinical trials for chemotherapeutic applications. Recently 9-cis retinoic acid has been identified as an additional endogenous retinoic acid isomer and a natural ligand for the retinoid X receptor (RXR). Therefore, 9-cis-retinoic acid is capable of modulating gene expression via this transcription factor.

Labelled retinoids are required for competitive binding studies with nuclear and cytosolic retinoid binding proteins and for metabolic studies in animals. The simplest route for making tritiated 9-cis-retinoic acid in small quantities is photochemical isomerization of commercially available [11, 12 $^3H_2$]RA. (M. I. Dawson, et al., *J. Labelled Compounds and Rediopharma.*, 2:345, 1993.) More recently Boehm, et al., *J. Med. Chem.* 37:408–414, 1994) reported the synthesis of [$^3H_2$] 9-cis-retinoic acid (specific activity 29 Ci/mmol) starting from ionylidene acetaldehyde.

[$^3H$] 9-cis-retinoic acid is commercially available from Amersham Life Science at 30–60 Ci/mmol.

An improved method for synthesizing 9-cis-retinoic acid, all trans-retinoic acid, 9-nor-retinoic acid and radiolabelled versions of these compounds is needed in the art.

SUMMARY OF THE INVENTION

The present invention is a method of synthesizing 9-cis-retinoic acid, all-trans-retinoic acid or 9-nor-retinoic acid. The method comprises the steps of adding a Grignard reagent of

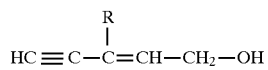

to 2,2,6 trimethyl cyclohexanone. R is a methyl group or H and the $CH_2$—OH group is in either the cis or trans orientation relative to the HC≡C- group. The resulting product is converted to retinoic acid.

In the preferable form of the present invention, a tritium-labelled retinoic acid is synthesized, wherein the labelling is at the $C_{20}$ position.

The present invention is also a preparation of tritium-labelled 9-cis-retinoic acid with a specific activity of greater than 65 Ci/mmol. In a most preferred embodiment, the specific activity is greater than 75 Ci/mmol.

It is an advantage of the present invention that a high specific activity preparation of radiolabelled retinoic acid, such as [$^3H$] 9-cis-retinoic acid, [$^3H$] all-trans-retinoic acid or [$^3H$] 9-nor-retinoic acid, is provided.

It is another advantage of the present invention that a retinoic acid preparation radioactively labelled at the $C_{20}$ position is provided.

Other objects, advantages and features of the present invention will become apparent after review of the specification, figures and claims.

DESCRIPTION OF THE INVENTION

In one embodiment, the present invention is a method of synthesizing 9-cis-retinoic acid, all-trans retinoic acid and 9-nor-retinoic acid. This method begins with the addition of a Grignard reagent of

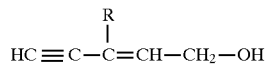

to commercially available 2,2,6 trimethyl cyclohexanone. In the compound described above, R is either a methyl group or H and the $CH_2$—OH group is in either the cis or trans orientation relative to the HC≡C- group. The product of this reaction is then converted to 9-cis-retinoic acid, all-trans retinoic acid or 9-nor-retinoic acid via organic synthesis methods described below and known in the art.

The method of the present invention is particularly advantageous in providing a radiolabelled retinoic acid compound wherein the radioactive label is at the $C_{20}$ position. The radioactive label may be attached to the $C_{20}$, such as when $^3H$ label is employed, or may substitute for the nonradioactive $C_{20}$ such as when $C_{14}$ label is employed.

Another embodiment of the present invention is a radiolabelled version of 9-cis-retinoic acid, all-trans-retinoic acid or 9-nor-retinoic acid. Preferably the labelled compound is tritium-labelled at $C_{20}$ and is of a specific activity in excess of 65 Ci/mmol. Most preferably, the specific activity is in excess of 75 Ci/mmol.

9-cis-retinoic acid

Poor yields and low specific activity of reported procedures and the need for high specific activity of radio-labelled 9-cis-retinoic acid (9-cis-RA) for biological studies prompted us to develop an improved method for the synthesis of 9-cis-RA. which can be used to isotopically label 9-cis-RA with high specific activity. Herein we report a novel synthesis of 9-cis-RA 1 (FIG. 1) and demonstrate the methodology for the preparation of deuterated 9-cis-RA. The method of the present invention is also suitable for the synthesis of all-trans-RA, 9-nor-RA and deuterated versions of these compounds. Tritiated versions of the retinoic acids can be prepared by substituting tritium-labeled intermediates for the deuterium-labelled intermediates described below.

Figure 1:
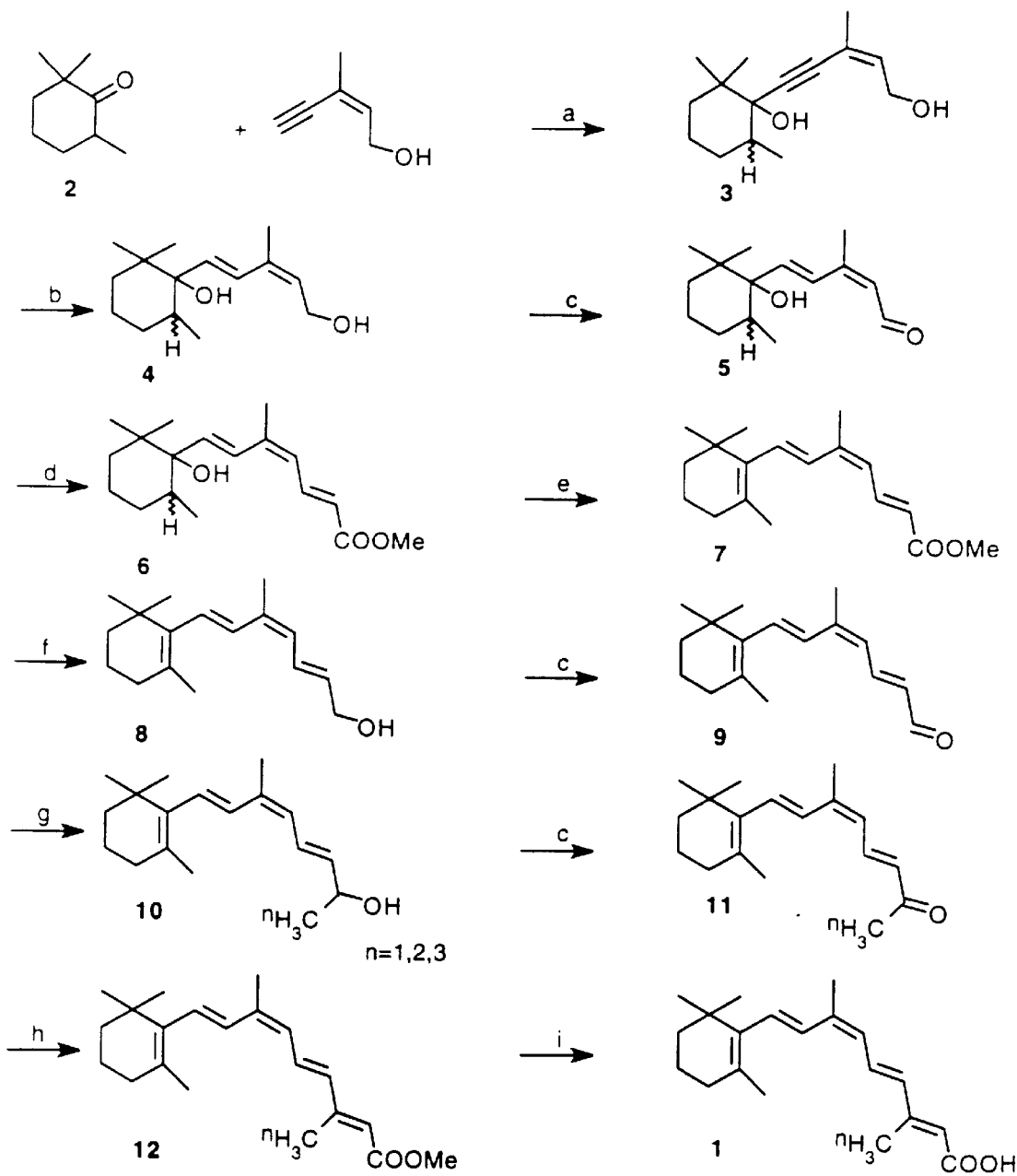
FIG. 1 is a schematic diagram of the synthesis of 9-cis-retinoic acid.
Figure 2:
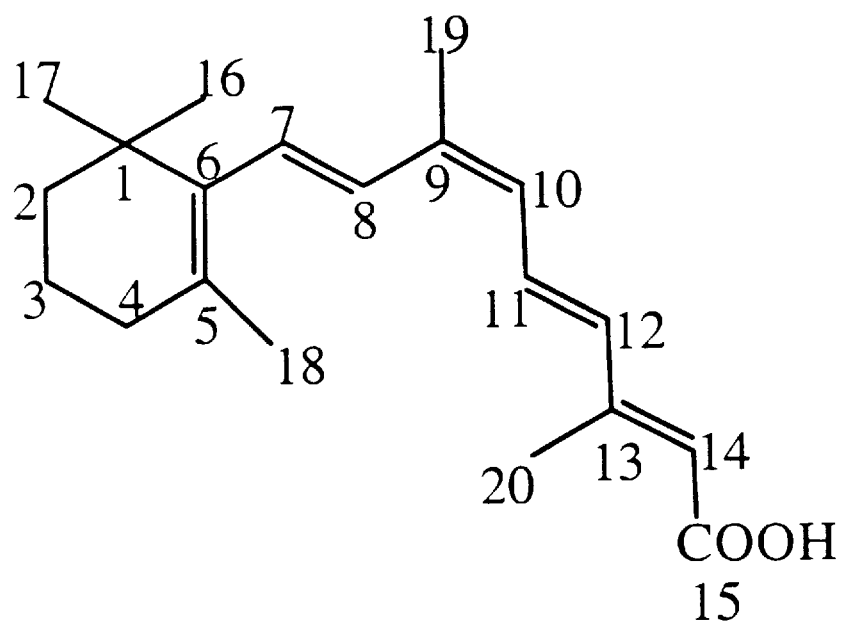
FIG. 2 is a numbered diagram of 9-cis-retinoic acid.

FIG. 1 is a schematic version of a preferred version of our method of synthesizing 9-cis-RA. FIG. 2 is a diagram of 9-cis-RA with numbered carbon positions.

Referring to FIG. 1, the method starts with commercially available 2,2,6 trimethyl cyclohexanone 2 (available from Aldrich.) Addition of Grignard reagent of (Z) 3-methyl-pent-2en-4ynol (purchased from Aldrich, Milwaukee, Wis.) affords the diastereomeric diols 3 (2(Z)-3-methyl-5-(1-hydroxy-2,2,6 trimethylcyclohexyl)-pent-2-en-4-ynol), typically in 80% yield. (G. L. Olson, et al., *Helv. Chim. Acta* 59:567, 1976.)

The mixture of diols 3 is reduced, preferably with lithium aluminum hydride (LAH) in tetrahydrofuran (THF), to yield dienols 4, typically with 68% yield. Because of the difficulties in generating a double bond in the ring by eliminating a tertiary hydroxyl group, we decided to keep the tertiary hydroxyl group as such and proceed further to create another double bond in the side-chain with subsequent elimination of tertiary hydroxyl group. We oxidize the primary hydroxyl group to an aldehyde (typically 79% yield), preferably using $MnO_2$ in (dry) dichloromethane (DCM). The aldehyde is subjected to wittig olefination using two carbon stable ylid in dry benzene to obtain compound 6, typically in 75% yield. Elimination of water is effected smoothly, preferably by treatment with 80% formic acid in hexane to yield $C_{17}$ ester 7, typically in 69% yield.

Compound 7 is reduced to its alcohol 8, preferably by using 2 equivalents of diisobutylaluminum hydride (DIBAL-H) in DCM at $-78°$ C., followed by oxidation to aldehyde 9, preferably with $MnO_2$ in DCM. The Grignard reagent of a methyl halide, preferably methyl bromide, is added to the aldehyde 9 to create alcohol 10, typically in 55% yield, which is further oxidized to ketone 11, preferably using $MnO_2$ in DCM.

Ketone 11 is then condensed with methyl-diethyl phosphono acetate (NaH, THF) to obtain methyl-(9Z)-retinoate in 52% yield. (J. D. Bu Lock, et al., *J. Labelled Compounds* 9:311–320, 1973.)

Finally, the ester is hydrolyzed, preferably using methanolic KOH, to afford a mixture of RA isomers, typically in 80% yield. Reverse-phase HPLC analysis will typically show four peaks. Three of the peaks coelute with pure 9-cis, 13-cis and all-trans-retinoic acid.

The major 9-cis isomer is selectively crystallized from MeOH. A preferable way to selectively crystallize the major isomer is to dissolve the material in methanol (MeOH) and subsequently cool the solution in an ice/salt bath or keep in a freezer. The melting point of the crystallized material may be correlated with previously reported data. (C. D. Robeson, et al., *J. Am. Chem. Soc.* 77:4111–4119, 1955.)

If one wished to identify the 9-nor compound or the all-trans compound, one would wish to characterize the compound by comparing its $^1$H NMR, MASS, or UV spectra to known values (see, for example, DeLera, et al. *Tetrahedron Letters* 33:6205–6208, 1992; Van Den Tempel, *Tetrahedron* 22:293–299, 1966).

Radiolabelled Retinoic Acid

The method of the present invention is suitable for producing retinoic acid radioactively labelled at the $C_{20}$ position. (FIG. 2 describes the numbered carbon positions of retinoic acid.) Preferable radiolabels include tritium and $C_{14}$.

Tritium-labelled retinoic acid is synthesized in an analogous manner to the 9-cis-retinoic acid described above except that $^3H_3CMgX$ is used in the Grignard reaction to obtain a tritiated alcohol. The alcohol is transformed into tritium-labelled $C_{20}$ RA by the same sequence of reactions used for the synthesis of 9-cis retinoic acid.

Specific activity is determined by counting the radioactivity of a sample of known concentration in a scintillation counter and then extrapulating the value for one millimole of substance. Preferably, one will obtain a specific activity greater than 65 Ci/mmole.

By anology, a $C_{14}$-labelled compound may be created by using a $C_{14}$-labelled substrate in the Grignard reaction described above. In this version of radio-labelling, it is the $C_{20}$ position that will be labelled directly.

All-trans-Retinoic Acid

Figure 3:
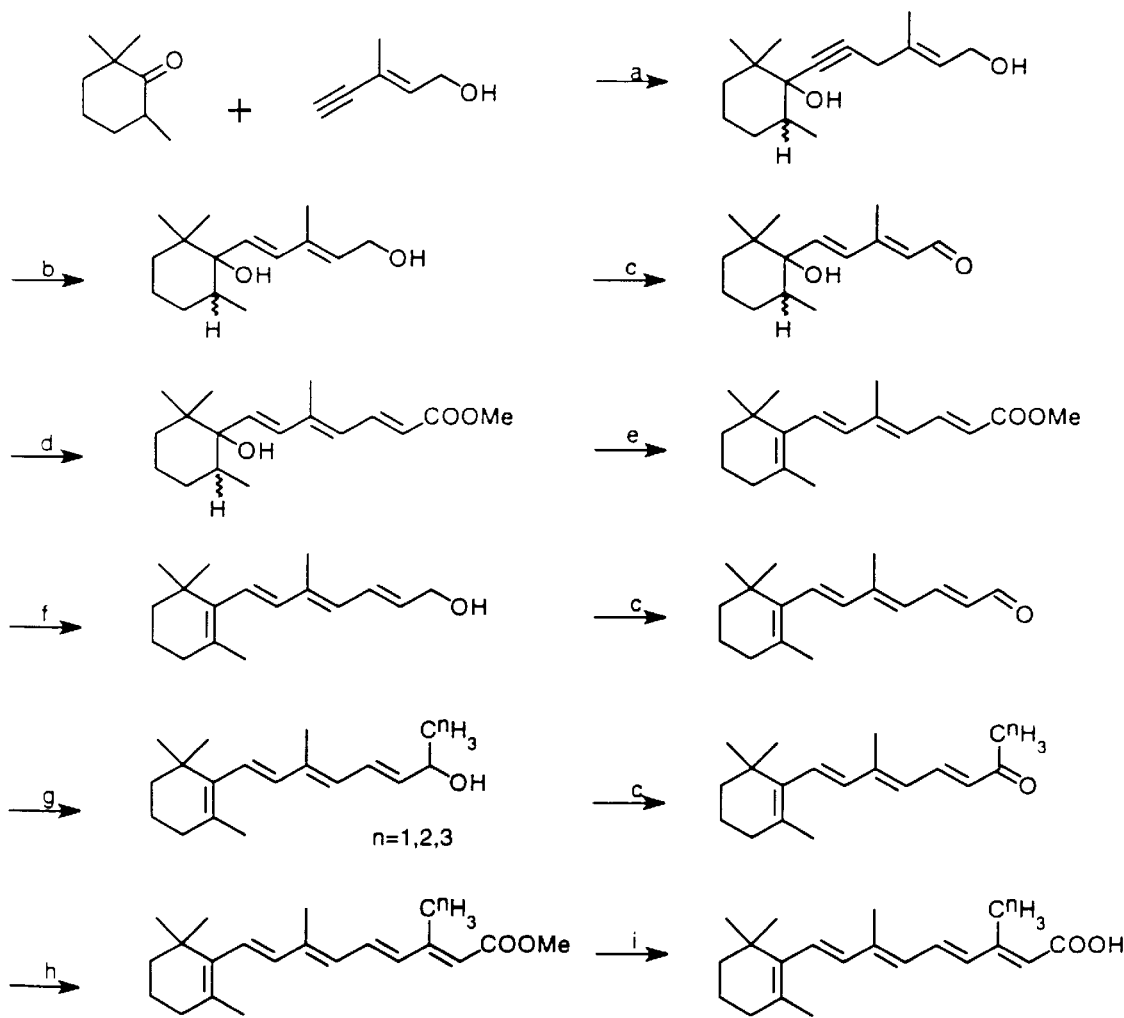
FIG. 3 is a schematic diagram of the synthesis of all-trans-retinoic acid.

The synthesis for all all-trans-retinoic acid is identical to that described above for 9-cis-retinoic acid except that (E) 3-methyl-pent-2en-4ynol is added in the first step. The reaction product would then be 2(E)-3methyl-5-(1-hydroxy-2,2,6 trimethylcyclohexyl)-pent-2-en-4-ynol. FIG. 3 describes this reaction. A radiolabelled version of all trans-retinoic acid is made identically to that described above for labelled 9-cis retinoic acid.

9-nor-Retinoic acid

The method of the present invention is also suitable for creating 9-nor-retinoic acid and a radiolabelled version of 9-nor-retinoic acid. (9-nor-RA lacks a methyl group at the $C_9$ position.) To create 9-nor-retinoic acid, one would begin with the addition of (E) or (Z)-3-pent-2en-4ynol to 2,2,6 trimethyl cyclehexanone 2 to produce either 2(E)-5-(1-hydroxy-2,2,6 trimethylcyclohexyl)-pent-2-en-4-ynol or 2(Z)-5-(1-hydroxy-2,2,6 trimethylcyclohexyl)-pent-2-en-4-ynol and proceed as described above.

Further Manipulation of the Synthesized Retinoic Acid

The present invention is also a method of creating labelled retinol and retinal. Retinoic acid can be converted into its alcohol via its methyl esters by reduction, preferably with DIBAL-H. The alcohol can then be converted to corresponding aldehyde, preferably by using $MnO_2$ oxidation. Therefore, one could create both labelled retinol and retinal from the method of the present invention.

In conclusion we have developed a convenient methodology for the synthesis of 9-cis-retinoic acid, all-trans-retinoic acid and 9-nor-retinoic acid. This method is also suitable for synthesizing tritium labelled 9-cis-retinoic acid, all trans-retinoic acid and 9-nor-retinoic acid with high specific activity. The method is also suitable for synthesizing labelled retinol and retinal.

EXAMPLES

Synthesis of 9-cis-retinoic acid
2(Z)-3 methyl-5-(1-hydroxy-2,2,6-trimethyl cyclohexyl)-pent-2-en-4-ynol (3):

To a stirred solution of 1.12 ml (1.5 equivalent) of (Z)-3 methyl-pent-2-en-4-ynol in 10 ml THF at 0° C. was added 7 ml of 3M etherial solution of ethylmagnesiumbromide (3 equiv.). The solution was stirred for 30 minutes at room temperature and then a solution of 1 g (1 equiv.) of 2,2,6 trimethyl cyclohexanone in 5 ml THF was added dropwise. The reaction mixture was stirred overnight and then quenched with saturated solution of $NH_4Cl$. Crude product was obtained after usual workup, which was further purified on a silicagel column using hexane and ethylacetate solvents to yield 1.35 g (80%) of product.
$^1$H NMR ($CDCl_3$):0.95 (3H,s,$CH_3$), 0.98 (3H,d,$CH_3$), 1.05 (3H,s,$CH_3$), 1.2–1.65 (6H,m,$CH_2$), 1.85 (3H,s,$CH_3$), 4.23 (2H,d,$CH_2OH$), 5.8 (1H,t,CH).

(2Z,4E)-3 methyl-5-(1-hydroxy-2,2,6-trimethyl cyclohexyl) -pent-2,4 dienol (4):

To a stirred mixture of LAH (0.218 g) in THF (10 ml) was added a solution of ynol 3 (1.35 g) in THF (5 ml) dropwise through a syringe. The reaction mixture was stirred overnight at room temperature. The flask was cooled to 0° C., excess of LAH was quenched with saturated solution of $Na_2SO_4$ and filtered through a celite pad. The residue was washed with dichloromethane several times and solvent was concentrated under reduced pressure. The mixture of dienols 4 were purified over silicagel column using hexane and ethylacetate solvents and 0.935 g. (68%) of product was obtained.

$^1$H NMR (CDCl$_3$):0.72 (3H,d,CH$_3$), 0.81 (3H,s,CH$_3$), 0.97 (3H,s,CH$_3$), 1.15–1.60 (6H,m,CH$_2$), 1.85 (3H,s,CH$_3$), 4.28 (2H,d,CH$_2$OH), 5.5 (1H,t,CH), 5.69 (1H,d,CH), 6.55 (1H, d,CH).

(2Z,4E)-3 methyl-5-(1-hydroxy-2,2,6-trimethyl cyclohexyl)-pent-2,4 diene-1-al (5):

To the mixture of dienol 4 (0.935 g) in 5 ml of dichloromethane was added 0.575 g of MnO$_2$. The reaction mixture was vigorously stirred at room temperature until the reaction was complete by TLC. After the completion of the reaction, the product was titered over a celite pad and the pad was washed with dichloromethane. The product (0.740 g, 79%) obtained after the concentration of solvent was used directly for the next reaction.

Methyl (2E,4Z,6E)-5 methyl-7-(1-hydroxy-2,2,6-trimethyl cyclohexyl -hepta-2,4,6 trienoate (6):

0.70 g of aldehyde 5 was dissolved in 10 ml of benzene and to it two carbon stable ylid 2.4 g was added. Stirring was continued until the reaction was completed. Solvent was removed under vacuum and the crude product was chromatographed to yield 0.650 g of hydroxy ester (75%).

$^1$H NMR (CDCl$_3$):0.75 (3H,d,CH$_3$), 0.82 (3H,s,CH$_3$), 1.10 (3H,s,CH$_3$), 1.21–1.64 (6H,m,CH$_2$), 1.92 (1H,m,tert.CH), 2.00 (3H,s,CH$_3$), 3.75 (3H,s,COOMe), 5.82 (1H,d,CH), 6.07 (1H,d,CH), 6.21 (1H,d,CH), 6.91 (1H,d,CH), 7.89 (1H,dd, CH).

Methyl (2E,4Z,6E)-5 methyl-7-(-2,2,6-trimethyl cyclohex-1-enyl)-hepta-2,4,6 trienoate (7):

To a solution of hydroxy ester 0.650 g in hexane were added 0.4 ml of 80% formic acid. The mixture was vigorously stirred at room temperature overnight. Isolation of the product in usual manner gave the dehydration product (0.39 g 69% yield).

$^1$H NMR (CDCl$_3$):1.02 (6H,s,2CH$_3$), 1.48 (2H,m,CH$_2$), 1.63 (2H,m,CH$_2$), 1.73 (3H,s,CH$_3$), 2.03 (3H,s,CH$_3$), 2.05 (2H, m,CH$_2$), 3.75 (3H,s,COOMe), 5.85 (1H,d,CH), 6.06 (1H,d, CH), 6.36 (1H,d,CH), 6.70 (1H,d,CH), 7.79 (1H,dd,CH).

Mass (m/z): 274 (M$^+$).

(2E,4Z,6E)-5 methyl-7-(-2,2,6-trimethyl cyclohex-1-enyl)-hepta-2,4,6 triene-1-ol (8):

To 0.350 g of ester 7 in 3 ml of dichloromethane at −78° C. was added 1.88 ml (1.5 molar solution) of DIBAL-H. The reaction mixture was stirred at −78° C. till the completion of the reaction (monitored by TLC). After the completion of the reaction, contents were poured into precooled solution of potassium sodium tartrate and extracted with dichloromethane. Combined layer of dichloromethane was washed with brine solution and dried over anhydrous Na$_2$SO$_4$. Solvent was removed under reduced pressure and pure compound 0.200 g (63%) yield was obtained after chromatographic purification.

$^1$H NMR (CDCl$_3$):1.00 (3H,s,CH$_3$), 1.13 (3H,s,CH$_3$), 1.50 (2H,m,CH$_2$), 1.58 (3H,s,CH$_3$), 1.65 (2H,m,CH$_2$), 1.72 (3H, s,CH$_3$), 2.05 (2H,m,CH$_2$), 4.24 (2H,bs,CH$_2$OH), 5.82 (1H, m,CH), 5.95 (1H,d,CH), 6.17 (1H,d,CH), 6.58 (1H,d,CH), 6.81 (1H,dd,CH).

Mass (m/z): 246 (M$^+$).

(2E,4Z,6E)-5 methyl-7-(-2,2,6-trimethyl cyclohex-1-enyl)-hepta-2,4,6 triene-1-al (9):

To 0.150 g of alcohol in 3 ml of dichloromethane was added 0.058 g of MnO$_2$. The reaction mixture was vigorously stirred at room temperature until the reaction was complete by TLC. After the completion of the reaction, product was filtered through celite pad and the celite pad was washed with dichloromethane. Solvent was removed under reduced pressure and pure compound 0.110 g, 74% yield was obtained after chromatographic purification.

Mass (m/z): 244 (M$^+$).

(2E,4Z,6E)-1,5 dimethyl-7-(-2,2,6-trimethyl cyclohex-1-enyl)-hepta-2,4,6 triene-1-ol (10a):

To a stirred solution of 0.100 g aldehyde in 2 ml THF at 0° C. was added 0.05 ml of MeMgBr. The solution was stirred for 30 minutes at 0° C. After the completion of the reaction, quenched with saturated solution of NH$_4$Cl and extracted with ether. Combined etherial layer was washed with water and brine solution and dried over anhydrous NaSO$_4$. Solvent was removed under vacuum and after chromatographic purification compound was obtained in 55% yield.

$^1$H NMR (CDCl$_3$):1.00 (6H,s,2CH$_3$), 1.30 (3H,d,CH$_3$), 1.45 (2H,m,CH$_2$), 1.56 (2H,m,CH$_2$), 1.73 (3H,s,CH$_3$), 1.94 (3H, s, CH$_3$), 2.01 (2H,m,CH$_2$), 4.41 (1H,d,CH$_2$OH), 5.66 (1H, dd,CH), 5.92 (1H,d,CH), 6.14 (1H,d,CH), 6.56 (1H,d,CH), 6.66 (1H,dd,CH).

Mass (m/z): 260 (M$^+$).

(2E,4Z,6E)-1,5 dimethyl-7-(-2,2,6-trimethyl cyclohex-1-enyl)-hepta-2,4,6 triene-1-one (11a):

To 0.050 g of alcohol in 2 ml of dichloromethane was added 0.018 g of MnO$_2$. The reaction mixture was vigorously stirred at room temperature until the reaction was complete by TLC. After the completion of the reaction the product was filtered through celite pad and the celite was washed with dichloromethane. Solvent was removed under vacuum and pure compound 0.039 g (79%) was obtained after chromatographic purification.

$^1$H NMR (CDCl$_3$):1.05 (6H,s,2CH$_3$), 1.50 (2H,m,CH$_2$), 1.65 (2H,m,CH$_2$), 1.75 (3H,s,CH$_3$), 2.00 (3H,s,CH$_3$), 2.05 (2H, m,CH$_2$), 2.25 (3H,s,CH$_3$), 6.05 (2H, two doublets merged, CH), 6.35 (1H,d,CH), 6.70 (1H,d,CH), 7.65 (1H,dd,CH).

Mass (m/z): 258 (M$^+$).

Methyl (2E,4Z,6Z,8E)-3,7 dimethyl-9-(-2,2,6-trimethyl cyclohex-1-enyl)-nona-2,4,6,8 trienoate (12a):

To a suspension of 50% dispersion of NaH in oil (4 mg) in THF was added 0.014 ml of methyl diethyl phosphono acetate and the reaction was stirred till cool and clear. Then 0.10 g of ketone in the THF was added dropwise and the reaction was stirred until the completion of the reaction at room temperature. Excess of NaH was quenched with water and the reaction mixture was extracted with ether. Etherial layer was washed with water, brine solution and dried over anhydrous Na$_2$SO$_4$. Solvent was distilled off under reduced pressure and chromatographic purification yielded methyl retinoate.

$^1$H NMR (CDCl$_3$):1.03 (6H,s,2CH$_3$), 1.46 (2H,m,CH$_2$), 1.62 (2H,m,CH$_2$), 1.73 (3H,s,18-CH$_3$), 2.00 (3H,s,19-CH$_3$), 2.07 (2H,m,CH$_2$), 2.34 (3H,s,20-CH$_3$), 3.71 (3H,s,COOCH$_3$), 5.77 (1H,s,14-CH), 6.03 (1H,d,10 or 12-CH), 6.21 (1H,d,10 or 12 CH), 6.28 (1H,d,8-CH), 6.66 (1H,d,7-CH), 7.09 (1H, dd,11-CH).

Mass (m/z): 314 M$^+$.

(2E,4Z,6Z,8E)-3,7 dimethyl-9-(-2,6,6-trimethyl cyclohex-1-enyl)-nona-2,4,6,8 tetraenoic acid (9-cis Retinoic acid) (1a):

To ester 12a in 5 ml of MeOH was added 0.5 ml of 5N KOH and the reaction mixture was heated to 60° C. for 1 hour. After the hydrolysis was complete (by TLC), the solution was cooled to 0° C. and acidified with 1N HCl. The organics were extracted with ether, dried over anhydrous Na$_2$SO$_4$ and concentrated in vacuo. The product was purified by crystallization to give pure 9-cis retinoic acid. The melting point of the crystallized product was 188°–190° C.

(See Robeson, et al, *Supra,* 1955 Reported at mp of 189°–190° C.).
$^1$H NMR (CDCl$_3$):1.06 (6H,s,2CH$_3$), 1.54 (2H,m,CH$_2$), 1.67 (2H,m,CH$_2$), 1.77 (3H,s,18-CH$_3$), 2.00 (3H,s,19-CH$_3$), 2.09 (2H,m,CH$_2$), 2.32 (3H,s,20-CH$_3$), 5.67 (1H,s,14-CH), 6.12 (1H,d,10-CH), 6.32 (2H,br,d,7CH+12CH), 6.71 (1H,d,8-CH), 7.13 (1H,dd,11-CH).
Mass (m/z): 300 M$^+$.
UV (Ethanol): 335 nm.

Synthesis of (20-CD$_3$)-9-Z-retinoic acid (20-CD$_3$) (2E,4E,6Z,8E)-3,7 dimethyl-9-(-2,6,6-trimethyl cyclohex-1-enyl)-nona-2,4,6,8 tetraenoic acid (9-cis retinoic acid) (1b):

(20-CD$_3$)-9-Z-retinoic acid was prepared in similar manner as 9-Z-retinoic acid except that in the Grignard reaction CD$_3$MgI was used instead of methyl magnesium bromide. 1H NMR spectra of 10b,11b,12b and 1b are similar to that of 10a,11a,12a and 1a except C-20 methyl signal is not there.
Mass m/z for 10b:263 M$^+$ 11b:261 M$^+$ 12b:317 M$^+$ 1b:303 M$^+$ Synthesis of 20-C$^3$H$_3$-9-Z-Retinoic Acid (20-C$^3$H$_3$)-9-Z-retinoic acid was prepared as described above except that C$^3$H$_3$MgI was used in the Grignard reaction. The specific activity of this preparation was 79.5 Ci/mmol.

We claim:

1. A method for synthesizing retinoic acid, comprising the steps of a) adding a Grignard reagent of

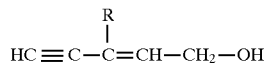

to 2,2,6 trimethyl cyclo hexanone, wherein R is a methyl group or H, and wherein the CH$_2$—OH group is in either the cis or trans orientation relative to HC≡C- group, and b) converting the resulting product to retinoic acid
wherein the conversion of step (b) comprises the following steps:

c) reducing the product of step (a), wherein a dienol is formed and wherein the dienol has a primary hydroxyl group, d) oxidizing the primary hydroxyl group, wherein an aldehyde is formed, e) subjecting the aldehyde of step (d) to wittig olefination using a two carbon stable ylid, f) eliminating water from the product of step (e), g) reducing the product of step (f), h) oxidizing the product of step (g), wherein an aldehyde is formed, i) adding a Grignard reagent of a methyl halide to the aldehyde of step (h), wherein an alcohol is formed, j) oxidizing the alcohol of step (i), wherein a ketone is formed, k) condensing the ketone of step (j) with methyl diethyl phosDhono acetate, and l) hydrolyzing the product of step (k), wherein a mixture of retinoic acid isomers is formed and wherein step (i) comprises adding a Grignard reagent of tritium-labelled methyl halide, whereby the retinoic acid of step (l) is tritium-labelled at the C$_{20}$ position.

2. The method of claim 1 wherein the tritium-labelled retinoic acid has a specific activity greater than 65 Ci/mmol.

3. The method of claim 2 wherein the specific activity is greater than 75 Ci/mmol.

4. The method of claim 1 wherein R is a methyl group and the CH$_2$—OH group is in the cis orientation.

5. The method of claim 1 wherein R is a methyl group and the CH$_2$—OH group is in the trans orientation.

6. The method of claim 1 further comprising the step of converting the product retinoic acid to its corresponding alcohol.

7. The method of claim 6 further comprising the step of converting the alcohol to an aldehyde.

8. A preparation of tritium-labelled retinoic acid, wherein the specific activity is greater than 65 Ci/mmol and wherein the retinoic acid is labelled at the C$_{20}$ position.

9. The preparation of claim 8 wherein the specific activity is greater than 75 Ci/mmol.

10. The preparation of claim 8 wherein the retinoic acid is selected from the group consisting of 9-cis-retinoic acid, all-trans-retinoic acid and 9-nor-retinoic acid.

11. A preparation of radiolabelled 9-cis-retinoic acid, wherein the retinoic acid is labelled at the C20 position and wherein the specific activity is greater than 65 Ci/mmol.

12. A preparation of radiolabelled all-trans-retinoic acid, wherein the retinoic acid is labelled at the C$_{20}$ position and wherein the specific activity is greater than 65 Ci/mmol.

13. A preparation of radiolabelled 9-nor-retinoic acid, wherein the retinoic acid is labelled at the C$_{20}$ position and wherein the specific activity is greater than 65 Ci/mmol.

* * * * *